(12) United States Patent
Davis et al.

(10) Patent No.: US 9,114,036 B2
(45) Date of Patent: Aug. 25, 2015

(54) DEVICE FOR AND METHOD OF LOADING STENTS INTO DELIVERY TUBES

(75) Inventors: Jake W. Davis, Flagstaff, AZ (US); Thomas J. Motsenbocker, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 385 days.

(21) Appl. No.: 13/528,409

(22) Filed: Jun. 20, 2012

(65) Prior Publication Data

US 2013/0152658 A1 Jun. 20, 2013

Related U.S. Application Data

(60) Provisional application No. 61/520,984, filed on Jun. 20, 2011.

(51) Int. Cl.
*B23P 11/00* (2006.01)
*A61F 2/95* (2013.01)
*B21C 5/00* (2006.01)

(52) U.S. Cl.
CPC ........... *A61F 2/95* (2013.01); *A61F 2002/9522* (2013.01); *B21C 5/00* (2013.01); *B21C 5/003* (2013.01); *Y10T 29/49927* (2015.01)

(58) Field of Classification Search
CPC ..... A61F 2/95; A61F 2002/9522; B21C 5/00; B21C 5/003; Y10T 29/49927
USPC .................. 29/505, 515, 516, 520, 282, 821; 72/370.12, 402; 623/901
See application file for complete search history.

(56) References Cited

U.S. PATENT DOCUMENTS

| 6,009,614 | A | 1/2000 | Morales |
| 2004/0148007 | A1 | 7/2004 | Jackson et al. |
| 2004/0181236 | A1 | 9/2004 | Eidenschink et al. |
| 2005/0154450 | A1 | 7/2005 | Larson et al. |
| 2006/0004469 | A1 | 1/2006 | Sokel |
| 2009/0299453 | A1 | 12/2009 | Arcand et al. |

FOREIGN PATENT DOCUMENTS

WO     02/11645 A2    2/2002

*Primary Examiner* — Ryan J Walters
(74) *Attorney, Agent, or Firm* — Thompson Coburn LLP (57) ABSTRACT

A stent loading device is configured to perform a method of loading a stent into a delivery tube that comprises loading a stent into an opening of a crimping device. The stent has an initial uncompressed diameter. The method further comprises crimping the stent via the crimping device in a manner reducing the diameter of the stent from the initial diameter. Still further, the method comprises forcing the stent out of the opening of the crimping device and into a passageway of a delivery tube while oscillating the crimping device. The passageway of the delivery tube has a diameter that is less than the initial diameter of the stent and receives the stent in its compressed state.

8 Claims, 7 Drawing Sheets

DEVICE FOR AND METHOD OF LOADING STENTS INTO DELIVERY TUBES

CROSS-REFERENCE TO RELATED APPLICATIONS

The application is a nonprovisional application and claims priority to U.S. Provisional Application Ser. No. 61/520,984, which was filed on Jun. 20, 2011, and which is hereby incorporated herein by reference in its entirety.

STATEMENT REGARDING FEDERALLY SPONSORED RESEARCH OR DEVELOPMENT

Not applicable.

APPENDIX

Not Applicable.

BACKGROUND OF THE INVENTION

1. Field of the Invention

The present invention pertains to devices and methods of compressing and loading stents into delivery tubes, such as catheters. More particularly, the present invention pertains to devices and methods that utilize vibrations or oscillations to reduce the friction required to forcibly insert radially compressed stents into delivery tubes. Using the present invention, a wider range of sizes and lengths of stents can be loaded into delivery tubes without being damaged during the process.

2. General Background

Several types of stents are commonly used to prevent blood vessels from collapsing. Such stents are typically radially compressed prior to insertion and are placed in delivery tubes that allow the stents to be passed through blood vessels during placement to minimize the evasiveness of the implantation procedures. Once properly positioned, the stents are forced out of the delivery tubes and radially expand to thereby maintain a fluid passageway through the blood vessels.

There are two primary types of stents. One type of stent is formed of traditional metal alloys and is radially expanded by inflating a balloon around which it was radially compressed. Once expanded, the balloon is deflated and withdrawn from the blood vessel. More recently, self-expanding stents have been used that utilize Shape Memory Alloys (SMA) to form stents that automatically expand when exposed to body temperature. An example of an SMA is nickel titanium alloy (typically referred to as nitinol). SMA stents are originally formed in their radially expanded state and must be radially compressed to be inserted into delivery tubes. When radially compressed, it can become difficult to load stents into delivery tubes without damaging the stents, due to the frictional forces resulting from the stents resiliency. Traditionally, radially compressed stents are either pulled or pushed into the delivery tubes. When frictional forces are high, the pushing or pulling forces can damage the stents.

To prevent damage to unique geometry and long stents during loading procedures, a so called "inchworm" technique is often used to load such stents into delivery tubes. Using that technique, rather than compressing the entire stent, small portions of the stent are reduced in diameter and are pushed into a delivery tube one portion at a time. This method requires skilled operators and normally greatly extends the loading time, thereby making it undesirable.

In view of the foregoing, prior art techniques of loading stents into delivery tubes have limitations and drawbacks.

SUMMARY OF THE INVENTION

The present invention overcomes some of the difficulties associated with loading stents into delivery tubes. The invention induces vibrations or oscillations in the crimping head of a stent loading device, which greatly reduces the force required to push or pull compressed stents into delivery tubes.

In one aspect of the invention, a method of loading a stent into a delivery tube comprises loading a stent into an opening of a crimping device. At this stage, the stent has an initial uncompressed diameter. The method further comprises crimping the stent via the crimping device in a manner reducing the diameter of the stent from the initial diameter. Still further, the method comprises forcing the stent out of the opening of the crimping device and into a passageway of a delivery tube while oscillating the diameter of the opening of the crimping device. The passageway of the delivery tube has a diameter that is less than the initial diameter of the stent and receives the stent in its compressed state.

In another aspect of the invention, a stent loading device comprises a crimping device, a stent extractor, and a programmable control system. The crimping device has a crimping device having an opening that is configured and adapted to receive a stent, the opening of the crimping device having an adjustable diameter. The stent extractor is configured and adapted to move linearly relative to the opening of the crimping device in a manner such that the stent extractor can force a stent out of the opening of the crimping device. The programmable control system can control the diameter of the opening of the crimping device and can control the linear movement of the stent extractor relative to the opening of the crimping device. The programmable control system is programed to oscillate the diameter of the opening of the crimping device and to simultaneously cause the stent extractor to move linearly relative to the opening of the crimping device.

In yet another aspect of the invention, a method of loading a stent into a delivery tube comprises loading a stent into an opening of a crimping device. At this stage, the stent has an initial uncompressed diameter. The method further comprises crimping the stent via the crimping device in a manner reducing the diameter of the stent from the initial diameter. Still further, the method comprises forcing the stent out of the opening of the crimping device and into a passageway of a delivery tube while oscillating the crimping device. The passageway of the delivery tube has a diameter that is less than the initial diameter of the stent and receives the stent in its compressed state.

Further features and advantages of the present invention, as well as the operation of the invention, are described in detail below with reference to the accompanying drawings.

Reference numerals in the written specification and in the drawing figures indicate corresponding items.

DETAILED DESCRIPTION

Figure 1:
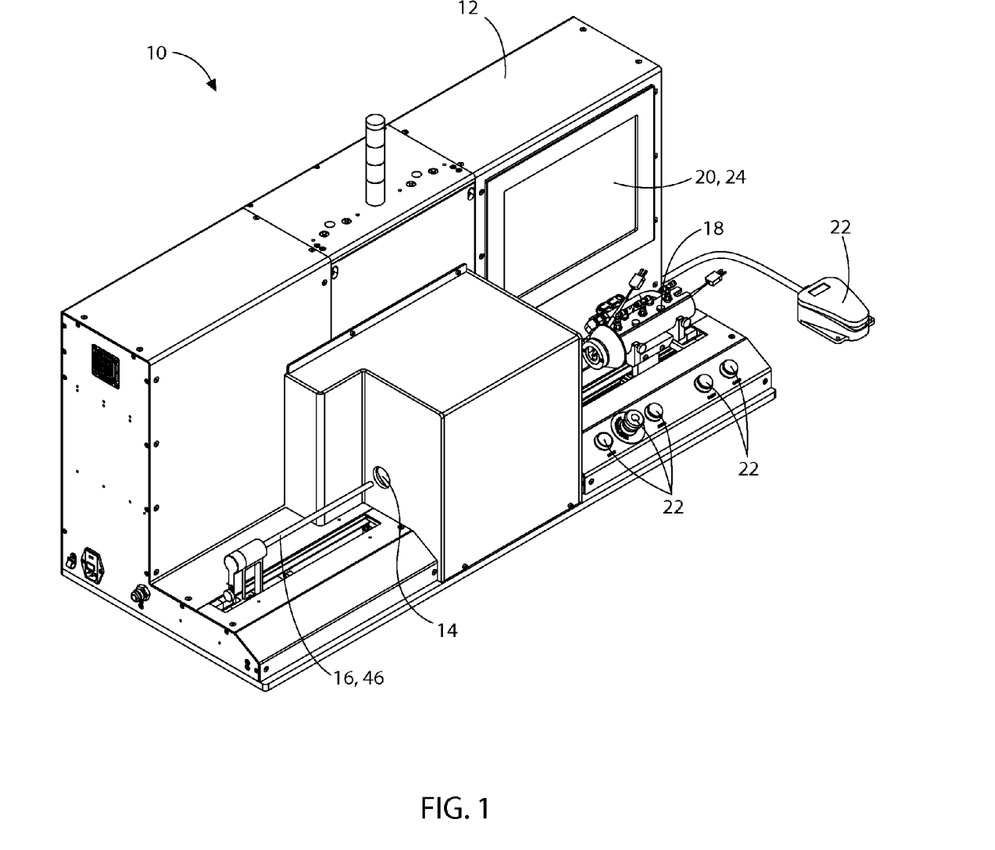
FIG. 1 depicts a perspective view of the preferred embodiment of a stent loading device in accordance with the invention, showing the front, left, and top sides thereof.
Figure 2:
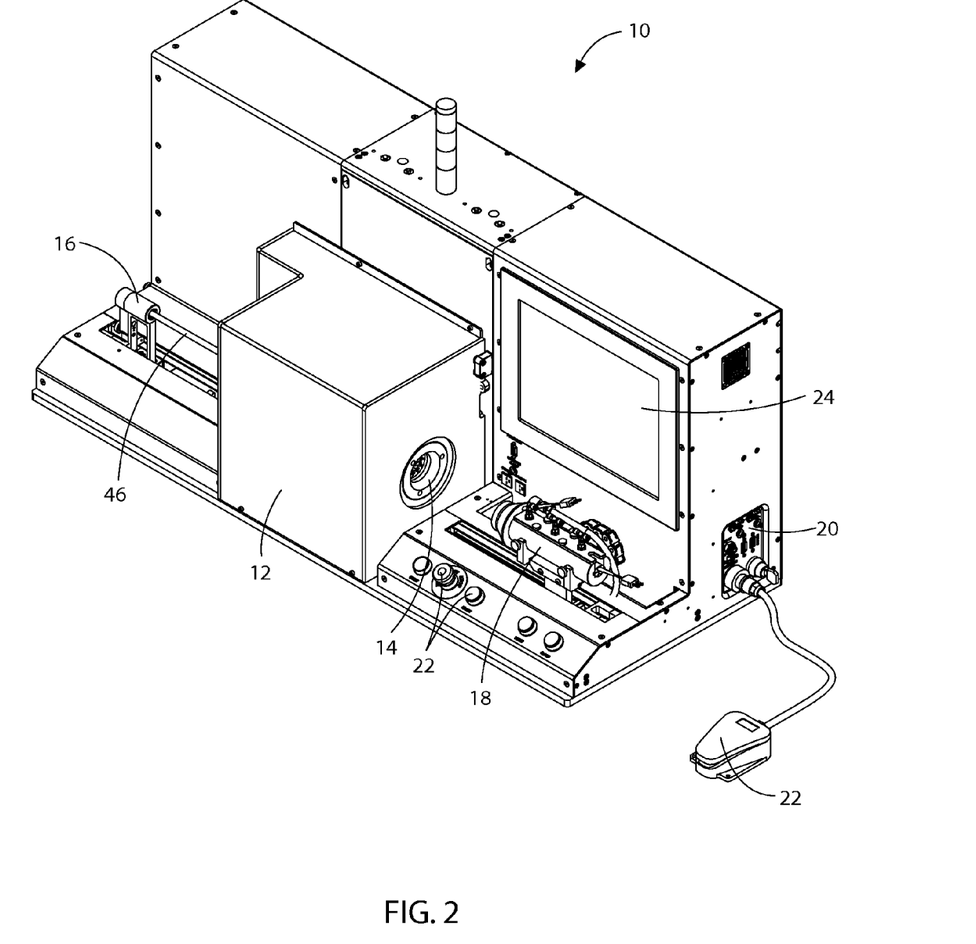
FIG. 2 depicts a perspective view of the stent loading device shown in FIG. 1, showing the front, right, and top sides thereof.
Figure 3:
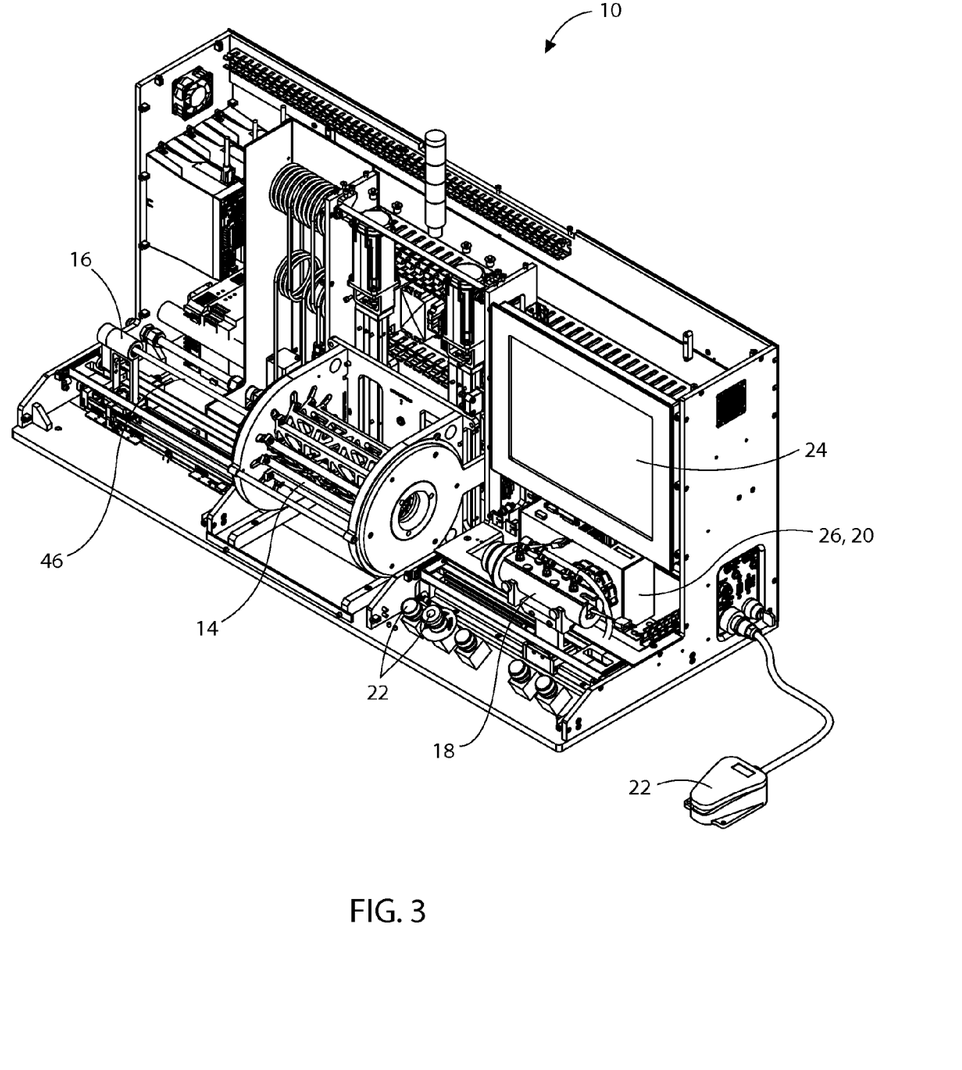
FIG. 3 is similar to FIG. 2 with the front and top housing panels removed from the stent loading device.
Figure 4:
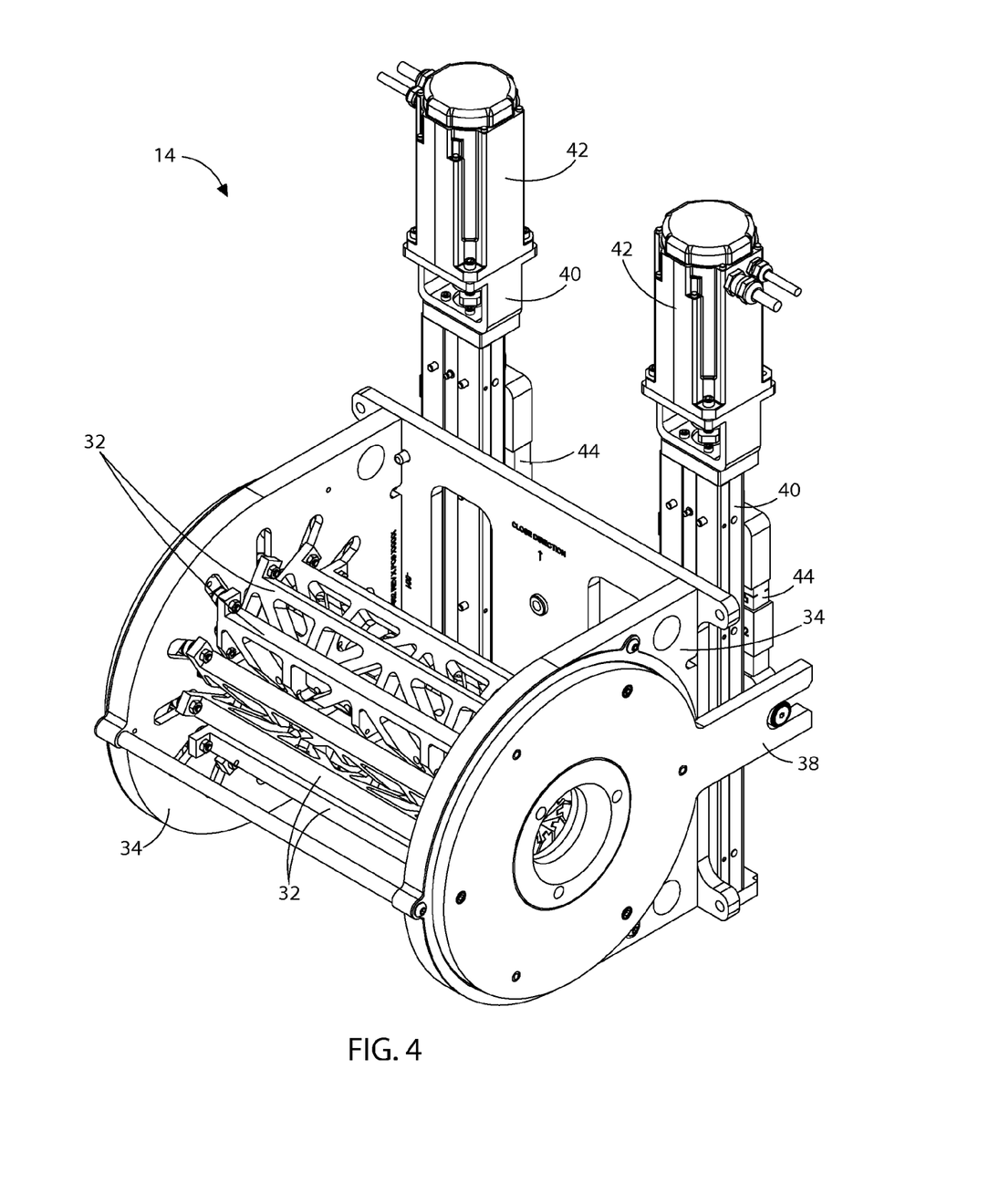
FIG. 4 depicts a perspective view of the crimping device showing the front, right, and top sides thereof.
Figure 5:
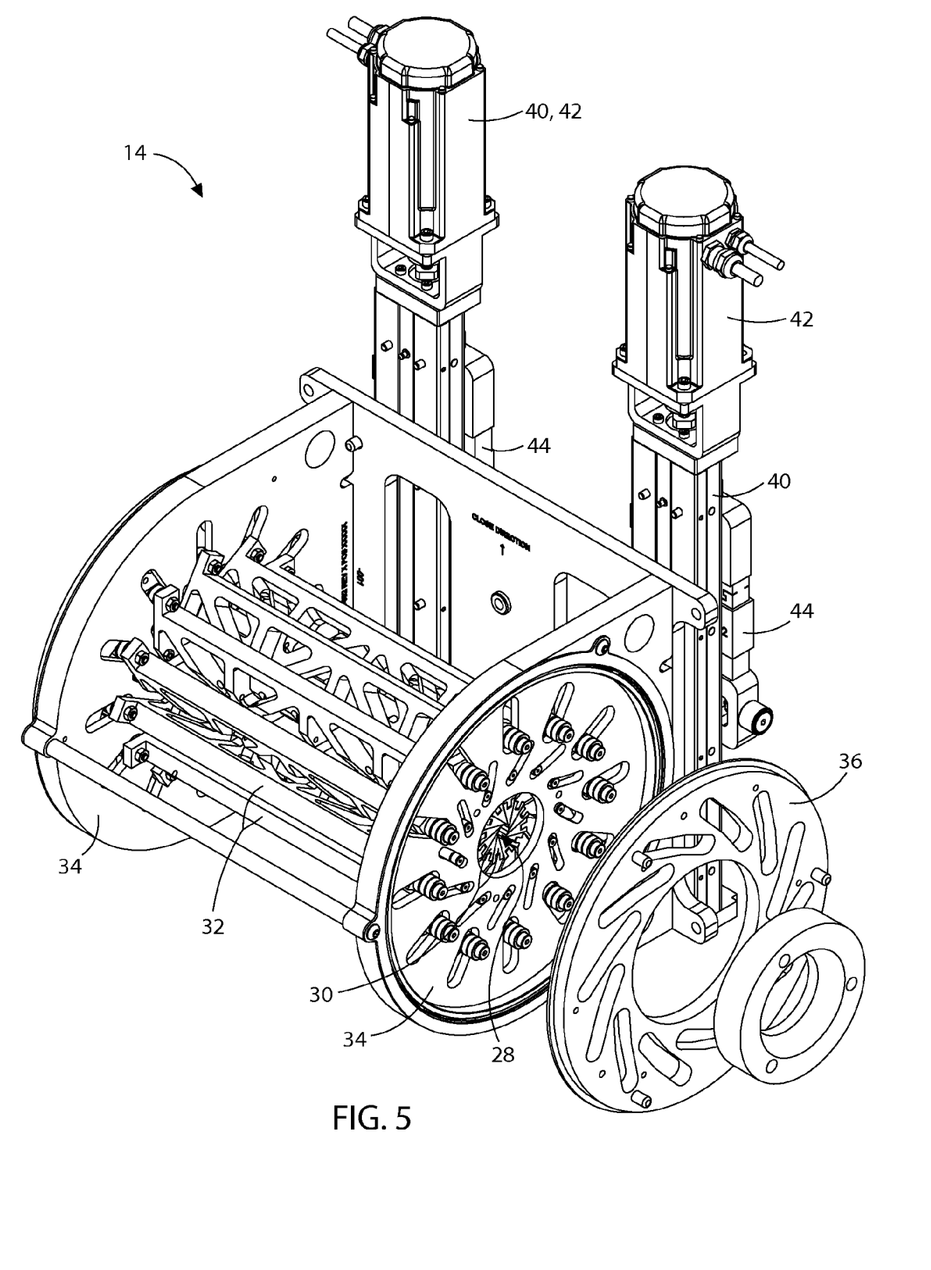
FIG. 5 is similar to FIG. 4 with some components removed and some shown in exploded view.
Figure 6:
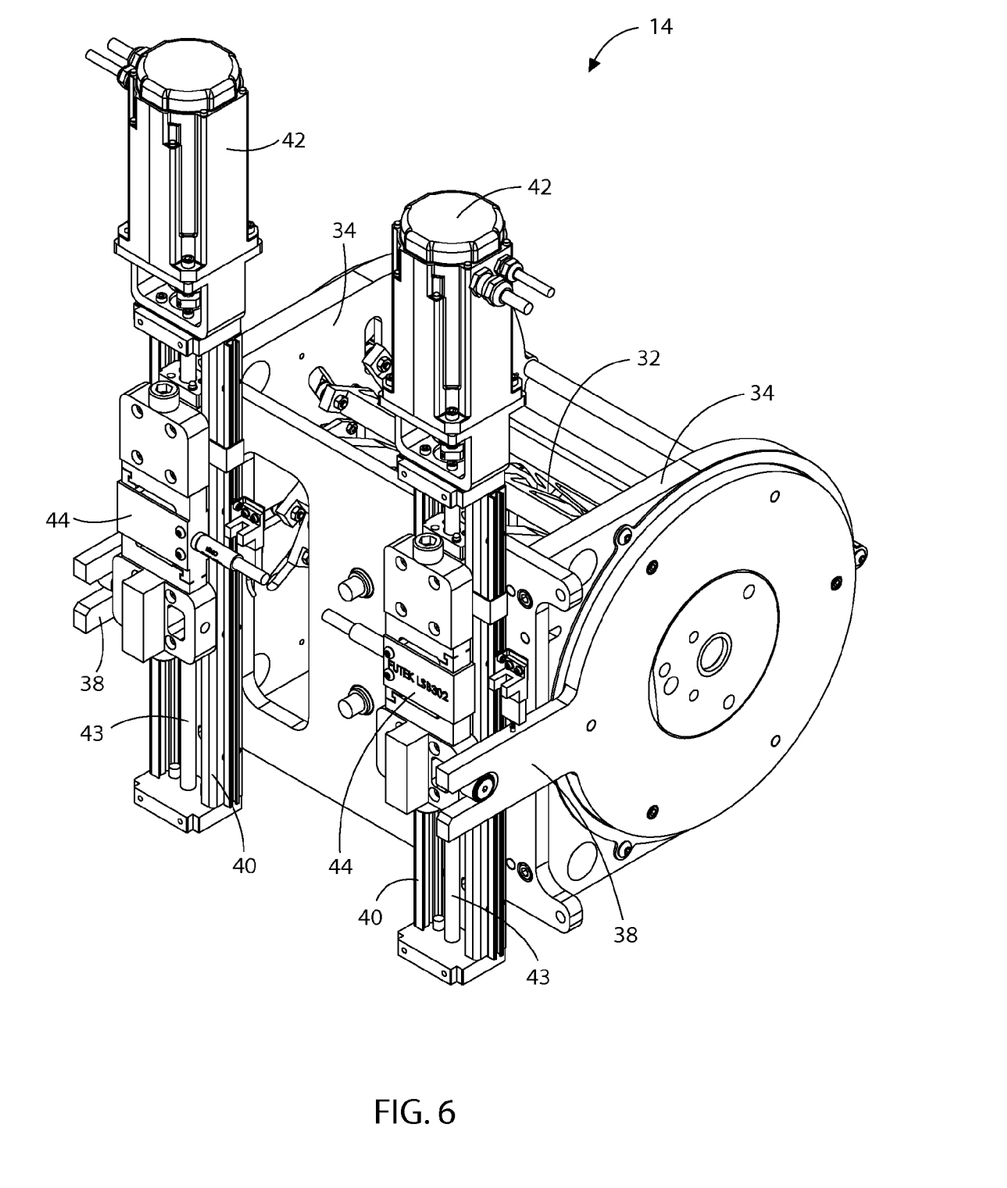
FIG. 6 depicts a perspective view of the crimping device showing the rear, left, and top sides thereof.
Figure 7:
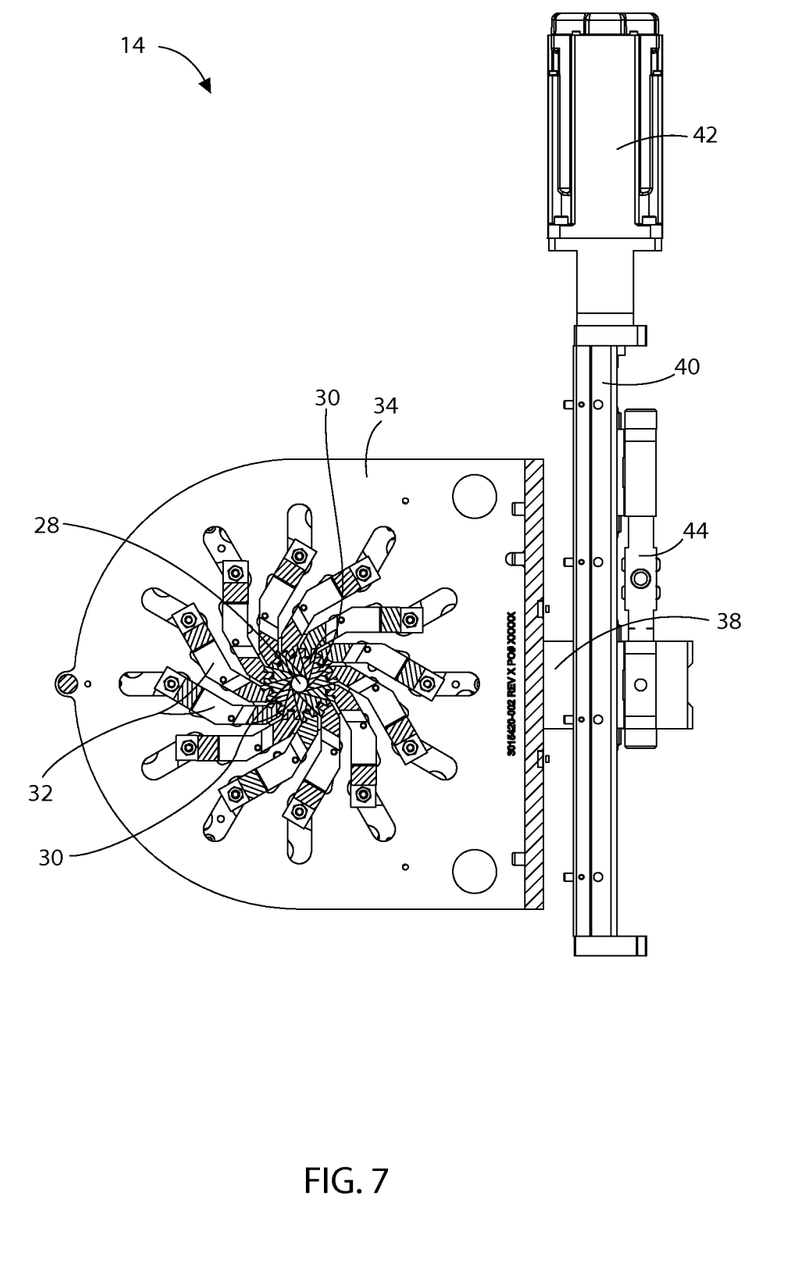
FIG. 7 depict a cross-section of the crimping device, taken down the middle of the device between its left and right sides.

A preferred embodiment of a stent loading device in accordance with the invention is shown in FIGS. 1 and 2. The stent loading device 10 comprises a housing 12, a crimping device 14, a stent extractor 16, and a delivery tube holder 18. The stent loading device 10 also comprises a programmable control system 20 (see FIG. 3) that is operatively connected to the crimping device 14, the stent extractor 16, and the delivery tube holder 18, and that comprises operating buttons 22, a digital display 24, and a central processing unit 26.

Like prior art stent loaders, the crimping device 14 is configured to receive a stent and to thereafter radially compress the stent. As such, the crimping device 14 has an adjustable diameter opening 28 (the cross-section of the opening actually has a dodecagon perimeter, and the term diameter as used herein should be interpreted to broadly cover any polygonal or segmented-arc perimeter opening). A plurality of movable wedge members 30 bound the opening 28 and are moved relative to each other by truss members 32. The opposite ends of the truss members 32 extend into a slotted fixed plate 34 and a pivotable slotted plate 36. The truss members 32 move radially in and out by pivoting the pivotable slotted plates 36 relative to the slotted fixed plates 34. Each of the pivotable slotted plates 36 is fixed to a crank 38 that extends radially outward therefrom. The end of each crank 38 is attached to a threaded linear actuator 40 that comprises a motor 42 that rotationally drives a threaded rod 43 (threads not shown). As the threaded rods 43 rotate, the cranks 38, along with the pivotable slotted plates 36 pivot about the opening 28 of the crimping device 14 in a manner adjusting the diameter of the opening. Preferably, a load cell 44 operatively connects the threaded rod 43 to its respective crank 38 in a manner such that the crimping force can be interpolated. The motors 42 preferably each comprise an internal sensor (not shown) that measures the rotation of the respective threaded rod 43. Data from the load cells 44 and other sensors are fed to the central processing unit 26 of the control system 20.

The stent extractor 16 comprises a quill rod 46 and is linearly moveable relative to the crimping device 14 along the axis of the crimping device's opening 28. The movement of the stent extractor 16 is controlled by the control system 20. The quill rod 46 has a diameter that is no greater than the compressed diameter of the stents being crimped. As such, the quill rod 46 can be moved into the opening 28 of the crimping device 14 when a stent is compressed in the crimping device and can therefore be used to push the stent out of the crimping device.

The delivery tube holder 18 lies adjacent the opposite side of the crimping device 14 and is configured to hold a catheter or other form of delivery tube (not shown) that is adapted to hold a stent in a compressed state until the stent is implanted. Like the stent extractor 16, delivery tube holder 18 is linearly moveable relative to the crimping device 14 along the axis of the crimping device's opening 28 such that a delivery tube can be positioned immediately adjacent the opening of the crimping device. As such, when the stent extractor 16 pushes a stent out of the crimping device 14, the stent moves into a delivery tube in its compressed state. The delivery tube holder 18 preferably includes a cooling system that is configured to counteract heat caused by friction so as to maintain SMA stents at temperatures below their shape memory temperatures during the loading process (the crimping device 14 may also comprise such a cooling system).

While the mechanical structure of the stent loading device 10 may not be novel, unlike prior art stent loading devices, the control system 20 of the device is programmed to oscillate the diameter of the opening 28 of the crimping device 14 as it moves the stent extractor 16 to force a stent out of the crimping device and into a delivery tube held in the delivery tube holder 18. To achieve that, the control system 20 causes the motors 42 of the threaded linear actuators 40 to rapidly change rotational direction. By doing this, the frictional forces between the crimping device 14 and a compressed stent held therein also oscillates and are therefore intermittently less than they otherwise would be. The reduced friction allows unique stent designs and longer length stents to be easily loaded without damaging the stents in the process. Oscillations in the frictional forces can also or alternatively be achieved by vibrating the crimping device 14 using pneumatic, acoustic, eccentric weight, or other common shakers/vibrators (not shown). Thus, "oscillating" the crimping device means moving portions of the crimping device relative to each other or shaking the entire crimping device. In either case, the frictional forces between a crimped stent and crimping device will also oscillate, thereby making it easier to force the stent out of the crimping device. However, direct oscillation of the diameter of the opening 28 of the crimping device 14 is preferred. The oscillations preferably occur at a rate in the range of 50 Hz to 1,000 Hz. The amplitude of the diametric oscillations is preferably between 0.001 and 0.006 inches. By programming the control system 20 to oscillate the rotation of the motors 42 of the threaded linear actuators 40 through a specific arc as measured by the internal sensors of the motors, the diameter of the opening 28 of the crimping device 14 can be precisely controlled, thereby preventing over-crimping the stents. In practice, the present invention reduces the forces required to push or pull compressed stents from the crimping device 14 by as much as fifty percent.

It should be appreciated that a stent loading device or method in accordance with this invention could be utilized to load non-SMA stents (such as balloon expanded stents). It should also be appreciated that a stent loading device or method in accordance with this invention could pull (rather than push) stents from a crimping device.

In view of the foregoing, it should be appreciated that the invention has several advantages over the prior art.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

It should also be understood that when introducing elements of the present invention in the claims or in the above description of exemplary embodiments of the invention, the terms "comprising," "including," and "having" are intended to be open-ended and mean that there may be additional elements other than the listed elements. Additionally, the term "portion" should be construed as meaning some or all of the item or element that it qualifies. Moreover, use of identifiers such as first, second, and third should not be construed in a manner imposing any relative position or time sequence between limitations. Still further, the order in which the steps of any method claim that follows are presented should not be construed in a manner limiting the order in which such steps must be performed, unless such and order is inherent.

What is claimed is:

1. A method of loading a stent into a delivery tube, the method comprising:

loading a stent into an opening of a crimping device of a stent loading device, the stent having an initial diameter, the opening having an adjustable size, the stent loading device comprising a control system and a motor driven threaded member that is functionally connected to the crimping device in a manner such that rotation of the motor driven threaded member controllably adjusts the size of the opening of the crimping device;

crimping the stent via the crimping device in a manner reducing the diameter of the stent from the initial diameter; and forcing the stent out of the opening of the crimping device and into a passageway of a delivery tube while oscillating the size of the opening of the crimping device, and thereby oscillating the stent, by rapidly changing rotational direction of the motor driven threaded member, the control system limiting the amplitude of the oscillations of the size of the opening of the crimping device by limiting the amount the threaded member rotates during the oscillations, the passageway of the delivery tube having a diameter that is less than the initial diameter of the stent.

2. A method in accordance with claim 1 wherein the control system is a programmable control system that monitors the amount the threaded member rotates during the oscillations.

3. A method in accordance with claim 1 wherein the stent loading device comprises a stent extractor that is controlled by the control system, and the forcing of the stent out of the opening of the crimping device is achieved via the stent extractor.

4. A method in accordance with claim 3 wherein the stent extractor comprises a rod and the forcing of the stent out of the opening of the crimping device is achieved by inserting the rod into the opening of the crimping device in a manner such that the rod pushes the stent out of the crimping device and into the passageway of the delivery tube.

5. A method in accordance with claim 3 wherein the stent extractor moves relative to the opening of the crimping device as the stent is forced out of the opening of the crimping device and into the passageway of the delivery tube, and the rate of the movement of the stent extractor is user adjustable.

6. A method in accordance with claim 1 wherein the stent comprises SMA material and the method further comprises chilling the delivery tube.

7. A method in accordance with claim 1 wherein the size of the opening of the crimping device is oscillated at a rate in the range of 50 Hz to 1,000 Hz.

8. A method in accordance with claim 1 wherein the step of forcing the stent out of the opening of the crimping device occurs in a continuous motion.

\* \* \* \* \*